United States Patent
Takeuchi (10) Patent No.: US 10,172,294 B2
(45) Date of Patent: Jan. 8, 2019

(54) METHOD FOR CULTIVATING PLANT

(71) Applicant: SHOWA DENKO K.K., Minato-ku, Tokyo (JP)

(72) Inventor: Ryouichi Takeuchi, Tokyo (JP)

(73) Assignee: SHOWA DENKO K.K., Minato-ku, Tokyo (JP)

( * ) Notice: Subject to any disclaimer, the term of this patent is extended or adjusted under 35 U.S.C. 154(b) by 315 days.

(21) Appl. No.: 14/171,069

(22) Filed: Feb. 3, 2014

(65) Prior Publication Data
US 2014/0215914 A1 Aug. 7, 2014

(30) Foreign Application Priority Data
Feb. 4, 2013 (JP) ................. 2013-019707

(51) Int. Cl.
*A01G 7/02* (2006.01)
*A01G 7/04* (2006.01)
*A01H 3/02* (2006.01)

(52) U.S. Cl.
CPC ............. *A01G 7/02* (2013.01); *A01G 7/045* (2013.01); *A01H 3/02* (2013.01); *Y02P 60/146* (2015.11)

(58) Field of Classification Search
CPC .......... A01G 9/20; A01G 7/045; A01G 31/02; A01G 9/18; A01H 3/02
See application file for complete search history.

(56) References Cited

U.S. PATENT DOCUMENTS

| | | | | |
|---|---|---|---|---|
| 3,673,733 A | * | 7/1972 | Allen | A01G 9/246 47/17 |
| 3,930,335 A | * | 1/1976 | Widmayer | A01G 7/045 47/58.1 R |
| 4,209,943 A | * | 7/1980 | Moeller | A01G 9/18 47/1.4 |
| 4,969,288 A | | 11/1990 | Mori | |
| 5,299,383 A | * | 4/1994 | Takakura | A01G 9/246 47/17 |

(Continued)

FOREIGN PATENT DOCUMENTS

CN 102758027 A 10/2012
CN 102986417 A 3/2013
(Continued)

OTHER PUBLICATIONS

Braddock et al. "Effects of Blue and Red Light on the Rate of Photosynthesis," Fall 2001. CU Boulder. as attached.*

(Continued)

*Primary Examiner* — Peter M Poon
*Assistant Examiner* — Morgan T Barlow
(74) *Attorney, Agent, or Firm* — Sughrue Mion, PLLC (57) ABSTRACT

A plant-cultivating method is provided which comprises a red light irradiation step (A) and a blue light irradiation step (B), wherein the step (A) and the step (B) are independently carried out for a predetermined period of time under cultivation conditions such that the concentration of carbon dioxide in a cultivation atmosphere at the step (B) is higher than that at the step (A). Preferably the concentrations of carbon dioxide at the step (B) and the step (A) are 1000-2500 ppm and 700-1500 ppm, respectively. The concentration of carbon dioxide at the step (B) is preferably at least 200 ppm higher than that at the step (A).

6 Claims, 2 Drawing Sheets

(56) References Cited

U.S. PATENT DOCUMENTS

| | | | | |
|---|---|---|---|---|
| 7,252,385 B2* | 8/2007 | Engle | ............... | G03B 21/16 353/52 |
| 2004/0109302 A1* | 6/2004 | Yoneda | ............... | A01G 7/045 362/2 |
| 2004/0233672 A1 | 11/2004 | Dubuc | | |
| 2005/0252078 A1* | 11/2005 | Albright | ............... | A01G 7/02 47/58.1 LS |
| 2006/0254135 A1 | 11/2006 | Dubuc | | |
| 2007/0151149 A1* | 7/2007 | Karpinski | ............... | A01G 7/045 47/58.1 LS |
| 2009/0151240 A1* | 6/2009 | Kayama | ............... | A01G 33/00 47/1.4 |
| 2010/0115830 A1* | 5/2010 | Dube | ............... | A01G 7/045 47/17 |
| 2011/0183368 A1* | 7/2011 | Chapman | ............... | A01G 7/045 435/29 |
| 2011/0252705 A1* | 10/2011 | Van Gemert | ............... | A01G 7/045 47/66.7 |
| 2012/0043907 A1* | 2/2012 | Lu | ............... | A01G 7/045 315/287 |
| 2012/0054061 A1 | 3/2012 | Fok et al. | | |
| 2012/0161170 A1* | 6/2012 | Dubuc | ............... | A01G 7/045 257/89 |
| 2012/0210637 A1* | 8/2012 | Kamahara | ............... | A01G 7/045 47/17 |
| 2012/0247013 A1 | 10/2012 | Sung | | |
| 2012/0260574 A1* | 10/2012 | Lin | ............... | A01K 1/02 47/66.6 |
| 2012/0293993 A1* | 11/2012 | Pan | ............... | A01G 7/045 362/231 |
| 2012/0310540 A1* | 12/2012 | McDermitt | ............... | G01N 21/6486 702/19 |
| 2013/0000185 A1 | 1/2013 | Tanase et al. | | |
| 2013/0139437 A1* | 6/2013 | Maxik | ............... | H05B 37/02 47/58.1 LS |
| 2013/0255150 A1* | 10/2013 | Karpinski | ............... | F21V 9/00 47/58.1 LS |
| 2013/0264934 A1* | 10/2013 | Osaki | ............... | A01G 7/045 313/46 |
| 2014/0215906 A1* | 8/2014 | Takeuchi | ............... | A01G 7/045 47/1.4 |
| 2014/0215912 A1* | 8/2014 | Takeuchi | ............... | A01H 3/02 47/58.1 LS |
| 2014/0215913 A1* | 8/2014 | Takeuchi | ............... | A01G 7/045 47/58.1 LS |
| 2014/0215914 A1* | 8/2014 | Takeuchi | ............... | A01H 3/02 47/58.1 LS |
| 2014/0215916 A1* | 8/2014 | Ara | ............... | A01H 3/02 47/58.1 LS |
| 2014/0215918 A1* | 8/2014 | Takeuchi | ............... | A01G 7/045 47/58.1 LS |
| 2014/0259920 A1* | 9/2014 | Wilson | ............... | A01G 7/045 47/62 R |
| 2014/0331555 A1 | 11/2014 | Nonomura | | |
| 2016/0007424 A1* | 1/2016 | Maxik | ............... | H05B 33/0854 315/153 |
| 2016/0007544 A1* | 1/2016 | Takashima | ............... | A01G 7/02 47/1.01 R |

FOREIGN PATENT DOCUMENTS

| | | | |
|---|---|---|---|
| EP | 0195431 A2 | 9/1986 | |
| EP | 1479286 A1 | 11/2004 | |
| JP | 06-276858 A | 10/1994 | |
| JP | 08-103167 A | 4/1996 | |
| JP | 11000066 A | 1/1999 | |
| JP | 2002272272 A | 9/2002 | |
| JP | 2005-52105 A | 3/2005 | |
| JP | 2006-67948 A | 3/2006 | |
| JP | 2008-142005 A | 6/2008 | |
| JP | 2011110028 A | 6/2011 | |
| JP | 2012-179009 A | 9/2012 | |
| JP | 2012249612 A | 12/2012 | |
| WO | 2009141287 A1 | 11/2009 | |
| WO | 2010044662 A1 | 4/2010 | |
| WO | WO 2013027198 A1 * | 2/2013 | ............... A01G 7/045 |

OTHER PUBLICATIONS

Green, Greg; "The Cannabis Grow Bible"; 2010, Green Candy Press.*

Assmann, Sarah M.; Enhancement of the Stomatal Response to Blue Light by Red Light, Reduced Intercellular Concentrations of $CO_2$, and Low Vapor Pressure Differences; Plant Physiology May 1988, 87 (1) 226-231; DOI: 10.1104/pp.87.1.226.*

Extended European Search Report dated Jun. 18, 2014, issued by the European Patent Office in corresponding application No. 14153578.1.

Communication dated Oct. 7, 2014 from the Japanese Patent Office in counterpart application No. 2013-019707.

Communication dated Jan. 22, 2016, issued by the U.S. Patent and Trademark Office in counterpart U.S. Appl. No. 14/170,806.

Communication dated Oct. 7, 2014, issued by the Japan Patent Office in counterpart Japanese Application No. 2013-019724.

Communication dated Jun. 18, 2014, issued by the European Patent Office in counterpart European Application No. 14153594.8.

* cited by examiner

METHOD FOR CULTIVATING PLANT

BACKGROUND OF THE INVENTION

(1) Field of the Invention

This invention relates to a method for cultivating a plant. More particularly it relates to a method for cultivating a plant while the plant is irradiated with an artificial light using a light-emitting lamp for plant cultivation whereby growth of the plant is promoted.

(2) Description of Related Art

Light-emitting technology has heretofore been adopted for growing seedlings or promoting growth of plants whereby a cultivation period of plants can be shortened and frequency of harvesting in the same farm can be increased. Plants can be grown to a large size within a predetermined period of time, and the crop yield can be enhanced.

As a plant cultivation technique utilizing artificial light irradiation, an illumination lamp facility for irradiating a plant alternately with green light and white light has been proposed, for example, in patent document 1. In this illumination lamp facility, plants are irradiated alternately with green light having a wavelength of 500 to 570 nm and white light having a wavelength of 300 to 800 nm whereby simulated day and night are created. Consequently the sugar translocation within plant bodies is smoothly effected and growth of plants is enhanced.

Another proposal has been proposed in patent document 2, which comprises an illumination lamp facility equipped with a light emitting diode (LED) for irradiating plants alternately or concurrently with blue light having a wavelength of 400-480 nm and red light having a wavelength of 620-700 nm to supply light energy for cultivation, growth, and tissue cultivation of plants. This illumination lamp facility is characterized as irradiating plants selectively with light having a wavelength corresponding to the light absorption peak of chlorophyll, i.e., in the vicinity of 450 nm and the vicinity of 660 nm whereby the plants are cultivated with an enhanced energy efficiency.

It is stipulated in patent document 2 that blue light and red light may be irradiated either concurrently or alternately (see patent document 2, claim 1). More specifically it is described in this patent document that single radiation of blue light, single radiation of red light and concurrent radiation of blue light and red light are compared with each other, and it was verified that the concurrent radiation of blue light and red light exhibited an enhanced effect on healthy growth of plants, which is similar to the growth achieved by sun light radiation, whereas the single radiation of blue light or red light brings about unhealthy growth such as spindly growth of plants (see patent document 2, paragraph [0011]). It is further described in patent document 2 that blue light and red light are alternately radiated by blinking by means of a blinking pattern at a high frequency of several megahertz or more (see patent document 2, paragraph [0006]).

However, patent document 2 is silent on a method of alternately conducting a blue light irradiation step and a red light irradiation step, and thus, growth promoting effects achieved by the alternate light irradiation method are not verified.

PRIOR ART DOCUMENTS

Patent Documents

Patent document 1: JP 1994-276858A
Patent document 2: JP 1996-103167A

To enhance the productivity in plant cultivation, a plant cultivation method utilizing artificial light irradiation, which is simple and easy, and exhibits enhanced energy effect and excellent growth promotion effect, is eagerly desired.

BRIEF SUMMARY OF THE INVENTION

A primary object of the present invention is to provide an improved method of cultivating a plant using an artificial light-irradiating facility, whereby the plant can be cultivated with more enhanced growth promotion effect.

The present inventor made extensive research for providing an improved method for cultivating a plant using an artificial light-irradiating lamp facility with more enhanced growth promotion effect, and have found that a plant-cultivation method comprising a step (A) of irradiating a plant with a red light and a step (B) of irradiating the plant with a blue light, wherein the two steps (A) and (B) are independently carried out for a predetermined period of time, exhibits an enhanced growth promotion effect, and further found that the growth promotion effect varies depending upon the cultivation conditions, especially the concentration of carbon dioxide in a cultivation atmosphere. Based on these findings, the present invention has been completed.

In accordance with the present invention, there are provided the following plant-cultivating methods.

(1). A method of cultivating a plant comprising a step (A) of irradiating the plant with a red light and a step (B) of irradiating the plant with a blue light, wherein the red light irradiation step (A) and the blue light irradiation step (B) are independently carried out for a predetermined period of time under cultivation conditions such that the concentration of carbon dioxide in a cultivation atmosphere at the blue light irradiation step (B) is higher than that at the red light irradiation step (A).

(2). The method of cultivating a plant as mentioned above in (1), wherein the concentration of carbon dioxide in a cultivation atmosphere at the blue light irradiation step (B) is in the range of 1,000 ppm to 2,500 ppm and the concentration of carbon dioxide in a cultivation atmosphere at the red light irradiation step (A) is in the range of 700 ppm to 1,500 ppm.

(3). The method of cultivating a plant as mentioned above in (1), wherein the concentration of carbon dioxide in a cultivation atmosphere at the blue light irradiation step (B) is at least 200 ppm higher than the concentration of carbon dioxide in a cultivation atmosphere at the red light irradiation step (A).

(4). The method of cultivating a plant as mentioned above in (1), wherein the concentration of carbon dioxide in a cultivation atmosphere at the blue light irradiation step (B) is maintained at a higher concentration than the concentration of carbon dioxide at the red light irradiation step (A) by allowing a stream of carbon dioxide-containing air to flow in the cultivation atmosphere at a flow rate in the range of 0.3 m/sec to 1 m/sec at the blue light irradiation step (B) and at a flow rate in the range of 0.1 m/sec to 0.6 m/sec at the red light irradiation step (A).

(5). The method of cultivating a plant as mentioned above in (4), wherein the flow rate of a stream of carbon dioxide-containing air at the blue light irradiation step (B) is at least 0.1 m/sec larger than the flow rate of a stream of carbon dioxide-containing air at the red light irradiation step (A).

(6). The method of cultivating a plant as mentioned above in (1), wherein the red light-irradiation step (A) and the blue light irradiation step (B) are alternately and repeatedly carried out over a period of at least one hour for each irradiation time.

(7). The method of cultivating a plant as mentioned above in (1), wherein the red light irradiation step (A) and the blue light irradiation step (B) are carried out using an illumination lamp facility having red light emitting elements and blue light emitting elements, both of which are capable of being independently operated, and the red light emitting elements and the blue light emitting elements exhibit a light emission intensity ratio of red light to blue light of at least 1:1 as expressed by a ratio of photosynthetic photon flux density of red light to blue light.

(8). The method of cultivating a plant as mentioned above in (7), wherein the red light emitting elements and the blue light emitting elements exhibit a light emission intensity ratio of red light to blue light in the range of 2:1 to 9:1 as expressed by a ratio of photosynthetic photon flux density of red light to blue light.

By the term "plant(s)" as used in this specification, we mean plants in a broad sense which include leaf plants, fruit plants such as strawberry and tomato, grains such as rice and wheat, and algae. The plants further include phytoplankton such as green algae, and mosses.

By independently carrying out the red light irradiation step (A) and the blue light irradiation step (B), and further controlling the carbon dioxide concentration in a cultivation atmosphere in the specific range in the plant-cultivation method comprising a red light irradiation step (A) and a blue light irradiation step (B) according to the present invention, an enhanced growth promotion effect can be achieved.

BRIEF DESCRIPTION OF THE DRAWINGS

FIG. 2, (a) through (d) are schematic plan views showing arrangements of red light emitting elements and blue light emitting elements in illumination lamps as used in the plant-cultivation method of the present invention, wherein the arrangements of light emitting elements are different from those in FIG. 1.

DETAILED DESCRIPTION OF THE INVENTION

Preferred modes for practicing the invention will be described with reference to the accompanying drawings. The described modes by no means limit the scope of the invention.

The plant cultivation method of the present invention is characterized by comprising a step (A) of irradiating the plant with a red light and a step (B) of irradiating the plant with a blue light, wherein the red light irradiation step (A) and the blue light irradiation step (B) are independently carried out for a predetermined period of time under cultivation conditions such that the concentration of carbon dioxide in a cultivation atmosphere at the blue light irradiation step (B) is higher than that at the red light irradiation step (A).

When red light and blue light are irradiated on a plant, the light absorption curve of chlorophyll has different peaks attributed to the red light and the blue light. Thus the red light and the blue light exhibit different functions. The red light is concerned with activation of phytochrome, and the blue light is concerned with activation of phototropin and cryptochrome. The present inventor has investigated the difference between the functions of red light and blue light in the growth of plants, and found that red light tends to enlarge the area of plant leaves.

It was further found that blue light tends to enhance the concentration of carbon dioxide in a cultivation atmosphere to a great extent as compared with the concentration of carbon dioxide enhanced by red light irradiation, and that, when air is supplied at a high rate to a cultivation atmosphere, blue light tends to enlarge the area of plant leaves and the thickness thereof.

Carbon dioxide is contained usually at a concentration of approximately 330 ppm in the air, and is indispensable for photosynthesis of plants. It is known that, when plants are cultivated in a facility with a confined space, the plant growth is enhanced by increasing the concentration of carbon dioxide in a cultivation atmosphere.

It is believed surprising that, when the red light irradiation step (A) and the blue light irradiation step (B) are independently carried out under cultivation conditions such that the concentration of carbon dioxide in a cultivation atmosphere at the blue light irradiation step (B) is higher than that at the red light irradiation step (A), a great growth promotion effect is achieved. The growth promotion effect can be conspicuously enhanced when the concentration of carbon dioxide is maintained within specific ranges, that is, when the concentration of carbon dioxide in a cultivation atmosphere at the blue light irradiation step (B) is in the range of 1,000 ppm to 2,500 ppm and the concentration of carbon dioxide in a cultivation atmosphere at the red light irradiation step (A) is in the range of 700 ppm to 1,500 ppm.

The reason for which the growth promotion effect is greatly enhanced by the plant cultivation method of the present invention is not clear, but, it is presumed that efficiency in the photosynthesis reaction of chlorophyll varies greatly depending upon the cultivation conditions, and respiration process of plants (i.e., the process by which plants convert sugars and oxygen into carbon dioxide) has a close relationship with the reaction processes of chlorophyll.

In the plant cultivation method of the present invention, the concentration of carbon dioxide in a cultivation atmosphere at the blue light irradiation step (B) is maintained preferably at a concentration of at least 200 ppm higher than the concentration of carbon dioxide in a cultivation atmosphere at the red light irradiation step (A).

It is preferable that the concentration of carbon dioxide in a cultivation atmosphere at the blue light irradiation step (B) is maintained at a higher concentration than the concentration of carbon dioxide at the red light irradiation step (A) while a stream of carbon dioxide-containing air is allowed to flow in the cultivation atmosphere at a flow rate in the range of 0.3 m/sec to 1 m/sec at the blue light irradiation step (B) and at a flow rate in the range of 0.1 m/sec to 0.6 m/sec at the red light irradiation step (A). By allowing a stream of carbon dioxide-containing air to flow in the cultivation atmosphere at the above-mentioned flow rates, carbon dioxide is adequately dispersed on plants and the photosynthesis process proceeds smoothly.

Preferably, a stream of carbon dioxide-containing air at the blue light irradiation step (B) is allowed to flow at a flow rate of at least 0.1 m/sec larger than the flow rate of a stream of carbon dioxide-containing air at the red light irradiation step (B).

Illumination Lamp for Plant Cultivation

In the plant cultivating method of the present invention, an illumination lamp facility for plant cultivation having red light emitting elements and blue light emitting elements, both of which are capable of being independently operated, is used for independently (preferably, alternately and repeatedly) carrying out the red light irradiation step (A) and the blue light irradiation step (B) for a predetermined period of time.

The illumination lamp facility is preferably provided with a control part capable of independently turning on and out the red light emitting elements and the blue light emitting elements. By the provision of the control part, the red light and the blue light can be irradiated alternately or concurrently, and for a desired period of time, depending upon the particular plant so as to attain the enhanced growth promotion effect.

The control part is preferably provided with a lamp controller (i.e., light emission intensity-controlling means) capable of controlling the light emission intensity ratio of red light to blue light. By the provision of the lamp controller, the light emission intensity ratio of red light to blue light can be controlled so as to attain more enhanced growth promotion effect.

Figure 1:
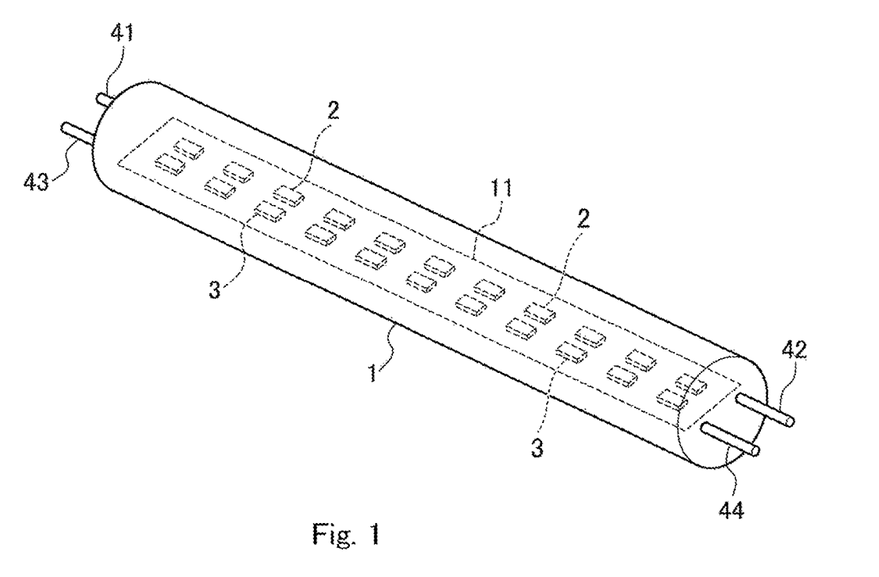
FIG. 1 is a perspective view of an example of an illumination lamp having red light emitting elements and blue light emitting elements as used in the plant-cultivation method of the present invention.

FIG. 1 is a perspective view of a preferable example of an illumination lamp for plant cultivation which has red light emitting elements and blue light emitting elements. This illumination lamp 1 has a light irradiation part 11 having a rectangular shape in the planar view, and further has a control part (not shown) for controlling the light irradiation part 11.

As illustrated in FIG. 1, the light irradiation part 11 is provided with plural red light emitting elements 2 and plural blue light emitting elements 3. In the plant cultivation lamp 1, as specifically illustrated in FIG. 1, the ratio in number of red light emitting elements 2 to blue light emitting elements 3 is 2:1.

Plural red light emitting elements 2 are arranged with equal intervals along a straight line extending in the length direction, and plural blue light emitting elements 3 are also arranged in a similar manner. The straight line of red light emitting elements 2 and the straight line of blue light emitting elements 3 are substantially parallel to each other.

The number of red light emitting elements 2 and the number of blue light emitting elements 3 may be the same or different in the illumination lamp 1, although the ratio in number of red light emitting elements to blue light emitting elements in the lamp illustrated in FIG. 1 is 2:1.

The rate of plant growth sometimes varies depending upon the light emission intensity ratio of red light and blue light. For example, some plants exhibit enhanced rate of growth when the red light emission intensity is larger than the blue light emission intensity. For these plants, it is preferable to use a plant cultivating illumination lamp 1 having a light emitting part provided with a larger number of red light emitting elements 2 than blue light emitting elements 3. By using the lamp 1 provided with a larger number of red light emitting elements 2 than blue light emitting elements 3, the light emission intensity of red light can be easily made larger than that of blue light.

For some plants, the light emission intensity of red light is preferably larger than that of blue light. Practically, for these plants, the light emission intensity ratio of red light to blue light (i.e., a ratio of the total emission intensity of red light to the total emission intensity of blue light) is preferably at least 1:1, more preferably in the range of 2:1 to 9:1, and especially preferably 2:1 to 5:1. It is preferable to use an illumination lamp having a light emitting part provided with a larger number of red light emitting elements than the number of blue light emitting elements, which part gives output beam having a light emission intensity ratio in the above-mentioned range when an appropriate current is applied to the respective red light emitting elements and blue light emitting elements.

The illumination lamp is preferably such that an applied electrical current can be exactly adjusted and the ratio of light emission intensity of red light to that of blue light can be desirably varied depending upon the particular kind of plant by precisely adjusting the electrical current.

If the ratio of light emission intensity of red light to that of blue light is smaller than the above-specified range, i.e., the blue light emission intensity is too large as compared with the red light emission intensity, the desired rate of growth is often difficult to attain. In contrast, if the ratio of red light emission intensity to blue light emission intensity is larger than the above-specified range, i.e., the red light emission intensity is too large, the desired rate of plant growth is also often difficult to attain, and, for example, undesirable growth such as spindly growth or overgrowth tends to occur.

As modification of the light irradiation part 11 of lamp 1 as illustrated in FIG. 1, which is provided with different numbers of red light emitting elements 2 and blue light emitting elements 3, various light emitting parts having red light emitting elements 2 and blue light emitting elements 3, which are arranged in different manners, can be used. Specific examples of the arrangement of red light emitting elements 2 and blue light emitting elements 3 in the light irradiation part 11 are illustrated in FIG. 2, (a) through (d).

Figure 2:
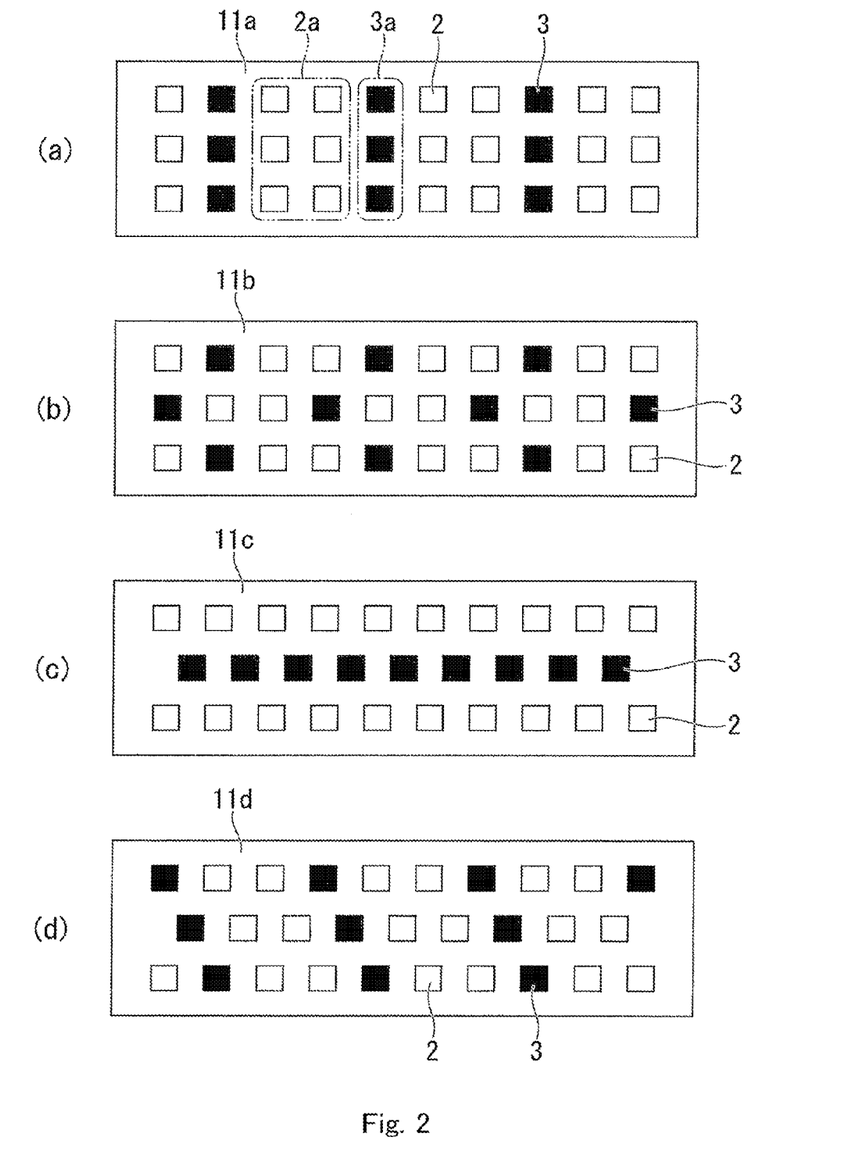

In FIG. 2, (a) through (d), each of light emitting parts 11a, 11b, 11c and 11d have red light emitting elements 2 and blue light emitting elements 3, the ratio in number of the elements 2 to the elements 3 is 2:1. In these figures, white square □ and black square ■ indicate red light emitting element 2 and blue light emitting element 3, respectively. The red light emitting elements 2 and the blue light emitting elements 3 are preferably arranged so that the distribution of light emission intensity is uniform over the entire light emission surface of each part 11a, 11b, 11c or 11d.

In the light irradiation part 11a as illustrated in FIG. 2 (a), light emitting elements 2 and 3 are regularly distributed to form plural rows each extending in parallel in the longitudinal direction of the light irradiation part 11a, and form plural columns each extending in parallel in the direction perpendicular to the plural rows. Along each of the plural rows, light emitting elements 2 and 3 are arranged at equal intervals so that a unit comprised of two red light emitting elements 2 and one blue light emitting element 1 repeatedly occurs along each row. Along each of the plural columns, plural red light emitting elements 2 or plural blue light emitting elements 3 are arranged at equal intervals. More specifically, in the arrangement as illustrated in FIG. 2 (a), three red light emitting elements 2 or three blue light emitting elements 3 are arranged at equal intervals along each column. In this arrangement, six red light emitting elements 2 are arranged in two adjacent columns to form a unit 2a, and three blue light emitting elements 3 are arranged in one row to form a unit 3a. The unit 2a of red light emitting elements 2 and the unit 3a of blue light emitting elements 3 are alternately arranged in the longitudinal direction of the light irradiation part 11a.

In the arrangement of light emitting elements 2 and 3 in the light irradiation part 11b as illustrated in FIG. 2 (b), these light emitting elements 2 and 3 are uniformly distributed to form plural rows each extending in parallel in the longitudinal direction of the light irradiation part 11b, and form plural columns each extending in parallel in the direction perpendicular to the plural rows. Along each of the plural rows, light emitting elements 2 and 3 are arranged at equal intervals so that a unit comprised of two red light emitting elements 2 and one blue light emitting element 1 repeatedly occurs along each row similarly to in FIG. 2 (*a*).

The irradiation part 11*b* as illustrated in FIG. 2 (*b*) includes three kinds of columns, which are comprised of (i) two red light emitting elements 2 and one blue light emitting element 1 sandwiched between the two red light emitting elements, (ii) two blue light emitting elements 3 and one red light emitting element 2 sandwiched between the two blue light emitting elements 3, and (iii) three red emitting elements 2, respectively. The three kinds of columns alternately occur in the longitudinal direction of the irradiation part 11*b*.

In the arrangement of light emitting elements 2 and 3 in the light irradiation part 11*c* as illustrated in FIG. 2 (*c*), plural light emitting elements 2 and 3 are uniformly distributed to form three rows each extending in parallel in the longitudinal direction of the light irradiation part 11*c*, that is, red light emitting elements 2 form two rows and blue light emitting elements form a single row, all of the rows extending in the longitudinal direction so that the single row of blue light emitting elements 3 is sandwiched between the two rows of red light emitting elements 2 in the light irradiation part 11*c*. Light emitting elements 2 or 3 in each row are arranged at equal intervals. In the arrangement illustrated in FIG. 2 (*c*), the blue light emitting elements 3 are arranged in a single row so that the center between two adjacent blue light emitting elements 3 is located approximately on a straight line connecting the center of two adjacent red light emitting elements 2 in one row to the center of two adjacent red light emitting elements 2 in another row.

In the arrangement of light emitting elements 2 and 3 in the light irradiation part 11*d* as illustrated in FIG. 2 (*d*), plural light emitting elements 2 and 3 are uniformly distributed to form three rows each extending in parallel in the longitudinal direction of the light irradiation part 11*d* so that a unit comprised of two red light emitting elements 2 and one blue light emitting element 3 repeatedly occurs in each row extending in the longitudinally extending direction, similarly to the light irradiation part 11*a* in FIG. 1 (*a*). Light emitting elements 2 and 3 in each row are arranged at equal intervals.

In the arrangement illustrated in FIG. 2 (*d*), the light emitting elements 2 and 3 occurring in the central row sandwiched between two rows are arranged so that the center between two adjacent light emitting elements is located approximately on a straight line connecting the center of two adjacent light emitting elements in one row to the center of two adjacent light emitting elements in another row. Each column comprised of three red light emitting elements 2 or three blue light emitting elements 3 appears inclined from the direction perpendicular to the longitudinal direction.

The light irradiation part of the illumination lamp facility as used in the present invention preferably has a mixed light emitting package such that red light emitting elements and blue light emitting elements are arranged in a single light emitting package. The mixed light emitting package preferably has a function such that the red light emitting elements and the blue light emitting elements are capable of being independently controlled.

The ratio of the light emission intensity of red light to the light emission intensity of blue light in the mixed light emitting package is preferably at least 1:1, more preferably in the range of 2:1 to 9:1, and especially preferably in the range of 2:1 to 5:1. By providing the light irradiation part with such mixed light emitting package, the red light emitting elements and the blue light emitting elements can be arranged with enhanced density in the light irradiation part.

Conventional red light emitting elements 2 and blue light emitting elements 3 can be used. For example, light emitting diode (LED) in which the desired wavelength can be easily selected and light energy within the effective wavelength region occupies a predominant part can be used. Laser diode (LD) and a electroluminescent (EL) element can also be used. The EL element used may be either an organic EL element or inorganic EL element.

Red light emitted from the red light emitting elements 2 has a wavelength in the range of 570 nm to 730 nm. Preferably the red light has a center emission wavelength within the range of 645 nm to 680 nm, and a wavelength in the range of the center emission wavelength±50 nm, more preferably the center emission wavelength±30 nm, and especially preferably the center emission wavelength±10 nm.

Blue light emitted from the blue light emitting elements 3 has a wavelength in the range of 400 nm to 515 nm. Preferably the red light has a center emission wavelength within the range of 410 nm to 510 nm, and a wavelength in the range of the center emission wavelength 450±30 nm, more preferably the center emission wavelength 450±20 nm, and especially preferably the center emission wavelength 450±10 nm.

The red light irradiated to a plant at the red light irradiating step (A) may include a minor proportion of lights other than red light, for example, blue light, provided that the total irradiated light exhibits a red light emission intensity ratio of at least 60%. According to the research of the present inventor, enhancement of plant growth at the red light irradiation step (A) can be observed when the total irradiated light exhibits a blue light emission intensity ratio of up to approximately 30%. The total irradiated light should preferably exhibit a blue light emission intensity ratio of up to approximately 20%, and most preferably zero. An example of the light irradiated to a plant at the red light irradiating step (A) exhibits a red light emission intensity ratio of 60%, a far-red light emission intensity ratio of 20% and a blue light emission intensity ratio of 20%. Most preferable example of the light irradiated at the red light irradiating step exhibits a red light emission intensity ratio of 100%.

The blue light irradiated to a plant at the blue light irradiating step (B) may include a minor proportion of lights other than blue light, for example, red light, provided that the total irradiated light exhibits a blue light emission intensity ratio of at least 60%. According to the research of the present inventor, enhancement of plant growth in the blue light irradiation step (B) can be observed when the total irradiated light exhibits a red light emission intensity of up to approximately 30%. The total irradiated light should preferably exhibit a red light emission intensity ratio of up to approximately 20%, and most preferably zero. An example of the light irradiated to a plant at the blue light irradiating step (B) exhibits a blue light emission intensity ratio of 60%, a far-red light emission intensity ratio of 20% and a red light emission intensity ratio of 20%. Most preferable example of the light irradiated at the blue light irradiating step exhibits a blue light emission intensity ratio of 100%.

By the term "light emission intensity ratio" as used in the specification, we mean those which are expressed by photosynthetic photon flux density (PPFD; in $\mu mol/m^2 s$).

The red light and the blue light, irradiated from the light irradiation part 11, preferably exhibit a photosynthetic photon flux density in the range of approximately 1 to 1000 μmol/m²s, more preferably approximately 10 to 500 μmol/m²s and especially preferably approximately 50 to 250 μmol/m²s.

The light emission intensity ratios of individual red light emitting elements and individual blue light emitting elements are not particularly limited, provided that the total red light emission intensity ratio of plural red light emitting elements and the total blue light emission intensity ratio of plural blue light emitting elements are within the above-mentioned range.

Illumination lamp facilities as preferably used for the plant cultivation are equipped with a control part. Emission intensities of red light and blue light, emitted from the irradiation part 11, can be controlled by varying the current value, applied to red light emitting elements 2 and blue light emitting elements 3, by the controlling part.

The plant cultivating illumination lamp 1 as illustrated in FIG. 1 is provided with a pair of electrodes 41 and 42 for red light emitting elements 2 and a pair of electrodes 43 and 44 for blue light emitting elements 3. The plural red light emitting elements 2 are electrically connected by wires (not shown) to the electrodes 41 and 42. The plural blue light emitting elements 3 are electrically connected by wires (not shown) to the electrodes 43 and 44.

The control part equipped in the illumination lamp facility 1 has a function of independently turning on and off the red light emitting elements 2 and the blue light emitting elements 3 by supplying electric current, respectively, via the electrodes 41 and 42 to the red light emitting elements 2 and via electrodes 43 and 44 to the blue light emitting elements 3.

The control part is provided with a lamp controller (i.e., light emission intensity-controlling means), which can turn on and off the red light emitting elements 2 and the blue light emitting elements 3 so that the red light and the blue light are irradiated alternately or concurrently, and for a desired period of time. Thus, the light emission intensity ratio of red light to blue light, irradiated from the light irradiation part 11, can be controlled so as to achieve the desired growth of plants.

The lamp controller used includes, for example, one type which can vary the light emission intensities of the red light emitting elements and the blue light emitting elements 3 by supplying different electric currents to a part or all of the red light emitting elements 2 and/or a part or all of the blue light emitting elements 3, thereby controlling the total emission intensity ratio of red light to blue light, irradiated from the light irradiation part 11; and another type which varies the light emission intensities of the red light emitting elements and the blue light emitting elements 3 by supplying an electric current only to a part of the red light emitting elements 2 and/or a part of the blue light emitting elements 3 to turn on a limited number of light emitting elements, thereby controlling the total emission intensity ratio of red light to blue light, irradiated from the light irradiation part 11.

In the plant cultivation lamp 1, as specifically disclosed in FIG. 1, provided with a light irradiation part 11 having the same number of red light emitting elements and blue light emitting elements, and with a lamp controller, the same electric current can be supplied to all of the red light emitting elements 2 and all of the blue light emitting elements 3, whereby red light and blue light which have the same light emission intensity are irradiated from the light irradiation part 11. Alternatively, a plant cultivation lamp 1 which is provided with a light irradiation part having the same number of red light emitting elements and blue light emitting elements, but is not provided with a lamp controller can be used in the case when the same electric current is supplied to all of the red light emitting elements 2 and all of the blue light emitting elements 3.

As another operation of the plant cultivation lamp 1, as illustrated in FIG. 1, provided with a light irradiation part having the same number of red light emitting elements and blue light emitting elements, and with a lamp controller, different currents can be supplied to the red light emitting elements 2 and the blue light emitting elements 3 so that the light irradiation part 11 irradiates light with an emission intensity ratio of red light to blue light being 2:1.

In the plant cultivation lamp provided with the light irradiation part 11a, 11b, 11c or 11d, as specifically disclosed in FIG. 2, which has twice as many red light emitting elements as blue light emitting elements, and with a lamp controller, the same current can be supplied to all of the red light emitting elements 2 and all of the blue light emitting elements 3 whereby the light irradiation part 11 irradiates light with an emission intensity ratio of red light to blue light being 2:1.

Alternatively, a plant cultivation lamp which is provided with a light irradiation part having twice as many red light emitting elements 2 as blue light emitting elements 3, but is not provided with a lamp controller, can be used in the case when the same electric current is supplied to all of the red light emitting elements 2 and all of the blue light emitting elements 3 whereby the light irradiation part 11 irradiates light with an emission intensity ratio of red light to blue light being 2:1.

As another operation of the plant cultivation lamp 1 provided with the light irradiation part 11a, 11b, 11c or 11d, as specifically disclosed in FIG. 2, which has twice as many red light emitting elements as blue light emitting elements, and with a lamp controller, twice current as large can be supplied to all of the red light emitting elements 2 as to all of the blue light emitting elements 3 whereby the light irradiation part 11 irradiates light with an emission intensity ratio of red light to blue light being 4:1 (red light/blue light).

The emission intensity ratio of red light to blue light, which are irradiated from the light irradiation part 11, is preferably at least 1:1, more preferably in the range of 2:1 to 9:1, and especially preferably in the range of 2:1 to 5:1, as mentioned above. In the case when the emission intensity ratio of red light to blue light is in this range, a highly enhanced plant growth can be attained by the sufficiently enhanced red light emission intensity as compared with the blue light emission intensity. When the emission intensity ratio of red light to blue light is smaller than the above-specified range, the desired high plant growth-enhancing effect is often difficult to attain. In contrast, when the emission intensity ratio of red light to blue light is larger than the above-specified range, the desired high plant growth-enhancing effect is also often difficult to attain and undesirable growth such as spindly growth sometimes occurs.

The provision of the light irradiation part having the red light emitting elements 2 and blue light emitting elements 3 is also advantageous as compared with the conventional illumination lamp facility having red light emitting means and blue light emitting means which are separately arranged, because the light emitting means can be easily and steadily arranged in the illumination lamp facility 1 and undesirable deviation of the irradiation directions of red light and blue light can be minimized.

The light irradiation part 11 as illustrated in FIG. 1 has a rectangular shape in a plan view, therefore, the illumination lamp facility 1 can be easily set in the position in which a conventional illumination facility such as straight tube fluorescent lamp is set.

The illumination lamp facility is preferably provided with a converter, built in the lamp, of converting alternating current to direct current for LED because of ease in setting and effective utilization of space. The terminal on one side and the terminal on the other side are preferably utilized separately for the red light emission and blue light emission in view of arrangement of electrical sources built therein and dispersion in generation of heat.

Further the illumination lamp facility is preferably provided with a dimmer for controlling LED in plural lamps and desirably adjusting the light emission intensity ratio.

Plant Cultivation Method

The method of cultivating a plant according to the present invention will now be explained specifically and more in detail on an embodiment using the illumination lamp 1 as illustrated in FIG. 1.

The plant cultivation method of the present invention comprises a step (A) of irradiating a plant with a red light (which is hereinafter referred to as "red light-irradiation step (A)" when appropriate) and a step (B) of irradiating a plant with a blue light (which is hereinafter referred to as "blue light irradiation step (B)" when appropriate), wherein the red light-irradiation step (A) and the blue light irradiation step (B) are independently carried out for a predetermined period of time.

By the term "independently" as used herein, we mean that the red light irradiation step (A) and the blue light irradiation step (B) exist separately in the course of plant cultivation.

The reason for which the desired enhanced growth of plant can be attained by independently carrying out the red light irradiation step (A) and the blue light irradiation step (B), as compared with a plant-cultivation method wherein red light and blue light are concurrently irradiated, is not clear. But, it is presumed that the photosynthesis process caused by the red light is different from that caused by the blue light due to the fact that chlorophyll exhibits a red light absorption peak distinct from a blue light absorption peak, therefore, when light and blue light are concurrently irradiated, the photosynthesis process by red light and the photosynthesis process by blue light undesirably interfere with each other.

By the term "predetermined period of time" as used herein, we mean an optional length of time within the course of plant cultivation. The maximum length of the predetermined period of time equals to the entire time length of the course of plant cultivation. The minimum length thereof can be voluntarily set provided that the desired plant growth-enhancing effect can be attained. The predetermined period of time can be expressed in unit of hour, day or minute depending upon the particular length of time.

Each of the red light irradiation step (A) and the blue light irradiation step (B) is carried out independently at least once, preferably at least two times, for the predetermined period of time. In the case when the red light irradiation step (A) and the blue light irradiation step (B) are carried out dividedly in two times or more, time length of each operation of the red light irradiation step (A) and time length of each operation of the blue light irradiation step (B) are preferably at least one hour, for example, 1 to 48 hours, and more preferably at least 3 hours, for example, 3 to 24 hours.

The red light irradiation step (A) and the blue light irradiation step (B) can be carried out either alternately and continuously, or intermittently with interposition of an operation of concurrently irradiating plant with red light and blue light between each operation of the red light irradiation step (A) and each operation of the blue light irradiation step (B), or with pause of irradiation between each operation of the red light irradiation step (A) and each operation of the blue light irradiation step (B).

Transfer between operation of red light irradiation step (A) and operation of red light irradiation step (A) can be conducted either instantaneously or over a certain length of time. The transfer may be conducted in stages. During the transfer, operation of red light irradiation step (A) and operation of red light irradiation step (A) may overlap with each other, or a pause of irradiation may intervene between operation of red light irradiation step (A) and operation of red light irradiation step (A).

Alternate flashing of red light irradiation and blue light irradiation by quickly repeating light flashing with a high frequency such as 1 Hz or higher is excluded from the light irradiation procedure adopted for independently carrying out the red light irradiation step (A) and the blue light irradiation step (B) for a predetermined period of time in the plant cultivation method of the present invention.

It is presumed that the mechanism of growth occurring due to light irradiation in the plant cultivation method of the present invention is different from the mechanism of growth occurring due to the alternate flashing of red light irradiation and blue light irradiation by quickly repeating light flashing with a high frequency such as 1 Hz or higher. In other words, in the case when operation of light irradiation is quickly repeated, the plant growth effect brought about by the flashed light irradiation would vary greatly depending upon each time length of light irradiation. In the plant cultivation method of the present invention, each operation for the red light-irradiation step (A) and each operation for the blue light irradiation step (B) are carried out for a period of time sufficient for allowing the photosynthesis reaction and related reactions to occur in connection with environmental changes to an extent such that the desired plant growth is achieved.

In contrast, in the alternate flashing of red light irradiation and blue light irradiation by quickly repeating light flashing with a high frequency such as 1 Hz or higher, the photosynthesis reaction and related reactions do not occur to the desired extent. This is because each flashing of red light irradiation and blue light irradiation occurs for a very short length of time which is insufficient for achieving the plant growth effect. The plant growth effect achieved by the alternate flashing is similar to that achieved by the operation of concurrently irradiating plant with red light and blue light.

The plant cultivation method of the present invention can be adopted for any period of time within the entire course of plant cultivation spanning from immediately after the germination of seeds or immediately after the plantation to the harvest.

In the plant cultivation method of the present invention, the red light-irradiation step (A) and the blue light irradiation step (B) are carried out under cultivation conditions such that the concentration of carbon dioxide in a cultivation atmosphere at the blue light irradiation step (B) is higher than that at the red-light irradiation step (A). The concentration of carbon dioxide in a cultivation atmosphere at the blue light irradiation step (B) is preferably in the range of 1000 ppm to 2500 ppm, more preferably 1200 ppm to 2000 ppm. The concentration of carbon dioxide in a cultivation atmosphere at the red-light irradiation step (A) is preferably in the range of 700 ppm to 1500 ppm, more preferably 800 ppm to 1200 ppm. The difference between the concentration of carbon dioxide in a cultivation atmosphere at the red-light irradiation step (A) and that at the blue light irradiation step (A) is preferably at least 2000 ppm.

The procedure by which the cultivation atmosphere with the desired concentration of carbon dioxide is realized is not particularly limited, and a conventional procedure can be adopted. A preferable procedure comprises supplying carbon dioxide from a gas cylinder at a predetermined flow rate to an air outlet port of an air conditioner, while the concentration of carbon dioxide in the air is measured by a carbon dioxide content meter, and the flow rate of carbon dioxide is controlled so that the stream of air flow having the desired $CO_2$ concentration is obtained.

The flow rate of carbon dioxide-containing air can be controlled by publicly known means, for example, by varying the number of revolution of an air-blowing fan or the damper opening.

It is preferable that the concentration of carbon dioxide in a cultivation atmosphere at the blue light irradiation step (B) is maintained at a higher concentration than the concentration of carbon dioxide at the red-light irradiation step (A) while a stream of carbon dioxide-containing air is allowed to flow in the cultivation atmosphere at a flow rate of 0.3 m/sec to 1 m/sec, preferably 0.5 m/sec to 0.8 m/sec, at the red-light irradiation step (B) and at a flow rate of 0.1 m/sec to 0.6 m/sec, preferably 0.3 m/sec to 0.5 m/sec, at the blue light irradiation step (A). By controlling the flow rate of a stream of carbon dioxide-containing air in the above-specified ranges, a desired amount of carbon dioxide spreads over the plants, and consequently the photosynthesis process of chlorophyll proceeds more smoothly.

The flow rate of a stream of carbon dioxide-containing air at the blue light irradiation step (B) is preferably at least 0.1 m/sec larger than the flow rate of a stream of carbon dioxide-containing air at the red-light irradiation step (A). The difference in the flow rate of a stream of carbon dioxide-containing air between the blue light irradiation step (B) and the red-light irradiation step (A) is more preferably in the range of 0.2 m/sec to 0.3 m/sec.

The plants to be cultivated in the method of the present invention are not particularly limited, and this term means plants in a broad sense which include leaf plants, root plants, fruit plants, pluses, grains, seeds, algae, house plants and mosses.

The plant cultivation method of the present invention should not be construed to be limited to the modes mentioned above.

The illumination lamp facility described above is equipped with a lamp controlling means for controlling light emission intensity. The plant cultivation can also be carried out using an illumination lamp facility not equipped with the lamp controlling means. This illumination lamp facility is advantageous in that a lamp controlling means and its accessories can be omitted and the cost of equipment production is reduced.

EXAMPLES

Preparation of Plants

In the following examples and comparative examples, leaf lettuce (variety: summer serge) was tested for observing the growth state.

Six seeds of leaf lettuce were sown at equal intervals in each test group on a peat van culture medium, and irradiated with fluorescent light for 12 hours of light per day to be thereby germinated. The seeds were placed under the same irradiation conditions over a period of three days spanning from seeding to germination. Thereafter seedlings were raised for seven days under irradiation with fluorescent light to give leaf lettuces for test.

Example 1

The raised seedlings of test leaf lettuces were placed in an environment control room wherein temperature-, humidity- and carbon dioxide concentration-controlling means were provided. The test leaf lettuces were cultivated under conditions of: atmosphere temperature of 25-27° C. and humidity of 60% RH, while the leaf lettuces were irradiated with red light and blue light as follows.

An illumination lamp for plant cultivation used had a light emitting part provided with 180 red light emitting elements and 60 blue light emitting elements. Each red light emitting element was comprised of a LED emitting red light having a center wavelength of 660 nm and a wavelength region of 640-680 nm, and each blue light emitting element was comprised of LED emitting blue light having a center wavelength of 450 nm and a wavelength region of 430-470 nm. The illumination lamp further had a control part for controlling the light emitting part so that the red light emitting elements and blue light emitting elements are independently turned on and off.

The red light emitting elements exhibited a total emission intensity, i.e., a total photosynthetic photon flux density (PPFD), of 150 $\mu mol/m^2 \cdot s$. The blue light emitting elements exhibited a total emission intensity, i.e., a total photosynthetic photon flux density (PPFD), of 50 $\mu mol/m^2 \cdot s$. Thus the total emission intensity ratio of red light to blue light was 3:1.

The red light-irradiation step and the blue light irradiation step were alternately and repeatedly carried out for 12 hours for each irradiation time per day, i.e., each light irradiation step was carried out separately and continuously over a period of 12 hours per day. There was no time for which the light irradiation was ceased.

The concentration of carbon dioxide in a cultivation atmosphere in the environment control room at the red light irradiation step was maintained at 1000 ppm by supplying a stream of air containing 1000 ppm of carbon dioxide at a flow rate of 0.4 m/sec. The concentration of carbon dioxide in a cultivation atmosphere in the environment control room at the blue light irradiation step was maintained at 1500 ppm by supplying a stream of air containing 1500 ppm of carbon dioxide at a flow rate of 0.6 m/sec.

When 20 days elapsed, the light irradiation was stopped and grown leaf lettuces were harvested. Ten leaves were collected from the periphery of each rolled lettuce, and average area of leaves, average thickness of leaves (each thickness was calculated by dividing the weight by the area), and fresh weight of the above-ground part of the lettuce were measured.

The measurement results are shown in Table 1. The cultivation results are expressed by relative indexes as the values in Example 1 being 100.

TABLE 1

| Examples, Comparative Examples | Ex. 1 | Ex. 2 | Ex. 3 | Ex. 4 | Ref. Ex. 1 | Ref. Ex 2 | Co. Ex. 1*[1] |
|---|---|---|---|---|---|---|---|
| Red light irradiation | | | | | | | |
| $CO_2$ concentration (ppm) | 1000 | 1000 | 1500 | 700 | 1000 | 1500 | 1500 |
| Flow rate of air stream (m/sec) | 0.4 | 0.5 | 0.6 | 0.2 | 0.4 | 0.4 | 0.4 |
| Blue light irradiation | | | | | | | |
| $CO_2$ concentration (ppm) | 1500 | 1500 | 2500 | 1000 | 1000 | 1500 | 1500 |
| Flow rate of air stream (m/sec) | 0.6 | 0.5 | 0.9 | 0.5 | 0.4 | 0.4 | 0.4 |
| Cultivation results *[2] | | | | | | | |
| Average area of leaves | 100 | 105 | 99 | 96 | 80 | 89 | 59 |
| Average thickness of leaves | 100 | 91 | 95 | 95 | 83 | 74 | 67 |
| Fresh weight of above-ground part | 100 | 94 | 94 | 93 | 86 | 81 | 49 |

Note;
*[1] In Comparative Example 1, red light and blue light were concurrently irradiated.
*[2] Relative indexes as vaues in Ex. 1 being 100

Example 2

By the same procedures as described in Example 1, leaf lettuces were cultivated except that the streams of carbon dioxide-containing air were supplied at a flow rate of 0.5 m/sec at both of the red light irradiation step and the blue light irradiation step over the entire cultivation process. All other cultivation conditions remained the same as in Example 1. The cultivation results are shown in Table 1.

Example 3

By the same procedures as described in Example 1, leaf lettuces were cultivated except that the concentration of carbon dioxide in a cultivation atmosphere in the environment control room at the red light irradiation step was maintained at 1500 ppm by supplying a stream of air containing 1500 ppm of carbon dioxide at a flow rate of 0.6 m/sec; and the concentration of carbon dioxide in a cultivation atmosphere in the environment control room at the blue light irradiation step was maintained at 2500 ppm by supplying a stream of air containing 2500 ppm of carbon dioxide at a flow rate of 0.9 m/sec. All other cultivation conditions remained the same as in Example 1. The cultivation results are shown in Table 1.

Example 4

By the same procedures as described in Example 1, leaf lettuces were cultivated except that the concentration of carbon dioxide in a cultivation atmosphere in the environment control room at the red light irradiation step was maintained at 700 ppm by supplying a stream of air containing 700 ppm of carbon dioxide at a flow rate of 0.2 m/sec; and the concentration of carbon dioxide in a cultivation atmosphere in the environment control room at the blue light irradiation step was maintained at 1000 ppm by supplying a stream of air containing 1000 ppm of carbon dioxide at a flow rate of 0.5 m/sec. All other cultivation conditions remained the same as in Example 1. The cultivation results are shown in Table 1.

Reference Example 1

By the same procedures as described in Example 1, leaf lettuces were cultivated except that the concentration of carbon dioxide in a cultivation atmosphere in the environment control room at both of the red light irradiation step and the blue light irradiation step was maintained at 1000 ppm by supplying a stream of air containing 1000 ppm of carbon dioxide at a flow rate of 0.4 m/sec over the entire cultivation process. All other cultivation conditions remained the same as in Example 1. The cultivation results are shown in Table 1.

Reference Example 2

By the same procedures as described in Example 1, leaf lettuces were cultivated except that the concentration of carbon dioxide in a cultivation atmosphere in the environment control room at both of the red light irradiation step and the blue light irradiation step was maintained at 1500 ppm by supplying a stream of air containing 1500 ppm of carbon dioxide at a flow rate of 0.4 m/sec over the entire cultivation process. All other cultivation conditions remained the same as in Example 1. The cultivation results are shown in Table 1.

Comparative Example 1

By the same procedures as described in Example 1, leaf lettuces were cultivated except that the red light irradiation step and the red light irradiation step were concurrently carried out; and the concentration of carbon dioxide in a cultivation atmosphere in the environment control room at both of the red light irradiation step and the blue light irradiation step was maintained at 1500 ppm by supplying a stream of air containing 1500 ppm of carbon dioxide at a flow rate of 0.4 m/sec over the entire cultivation process. All other cultivation conditions remained the same as in Example 1. The cultivation results are shown in Table 1.

The invention claimed is:
1. A method of cultivating a plant using only artificial lights and comprising;
   a step (A) of irradiating the plant with a red light and
   a step (B) of irradiating the plant with a blue light, to enhance growth promotion effect,
   wherein the red light-irradiation step (A) and the blue light irradiation step (B) are independently carried out for a predetermined period of time under cultivation conditions such that a concentration of carbon dioxide in a cultivation atmosphere at the blue light irradiation step (B) is higher than that at the red light irradiation step (A),
   wherein the concentration of carbon dioxide in a cultivation atmosphere at the blue light irradiation step (B) is controlled by supplying carbon dioxide at a predetermined flow rate, while the concentration of carbon dioxide in the air is measured, and the flow rate of carbon dioxide is controlled so that the concentration is in the range of 1,000 ppm to 2,500 ppm and the concentration of carbon dioxide in a cultivation atmosphere at the red-light irradiation step (A) is controlled by supplying carbon dioxide at a predetermined flow rate, while the concentration of carbon dioxide in the air is measured, and the flow rate of carbon dioxide is controlled so that the concentration is in the range of 700 ppm to 1,500 ppm, and wherein time length of each predetermined period of time for the red light irradiation step (A) and time length of each predetermined period of time for the blue light irradiation step (B) are 3 to 48 hours, respectively.

2. The method of cultivating a plant according to claim 1, wherein the concentration of carbon dioxide in a cultivation atmosphere at the blue light irradiation step (B) is at least 200 ppm higher than the concentration of carbon dioxide in a cultivation atmosphere at the red-light irradiation step (A).

3. The method of cultivating a plant according to claim 1, wherein the concentration of carbon dioxide in a cultivation atmosphere at the blue light irradiation step (B) is maintained at a higher concentration than the concentration of carbon dioxide at the red-light irradiation step (A) while a stream of carbon dioxide-containing air is supplied in the cultivation atmosphere at a flow rate in the range of 0.3 m/sec to 1 m/sec at the blue light irradiation step (B) and at a flow rate in the range of 0.1 m/sec to 0.6 m/sec at the red light irradiation step (A).

4. The method of cultivating a plant according to claim 3, wherein the flow rate of a stream of carbon dioxide-containing air at the blue light irradiation step (B) is at least 0.1 m/sec larger than the flow rate of a stream of carbon dioxide-containing air at the red light irradiation step (A).

5. The method of cultivating a plant according to claim 1, wherein the red light irradiation step (A) and the blue light irradiation step (B) are carried out using an illumination lamp facility having red light emitting elements and blue light emitting elements, both of which are capable of being independently operated, and the red light emitting elements and the blue light emitting elements exhibit a light emission intensity ratio of red light to blue light of at least 1:1 as expressed by a ratio of photosynthetic photon flux density of red light to blue light.

6. The method of cultivating a plant according to claim 5, wherein the red light emitting elements and the blue light emitting elements exhibit a light emission intensity ratio of red light to blue light in the range of 2:1 to 9:1 as expressed by a ratio of photosynthetic photon flux density of red light to blue light.

* * * * *